United States Patent [19]

Brachwitz et al.

[11] Patent Number: 5,155,099

[45] Date of Patent: Oct. 13, 1992

[54] ALKYLPHOSPHONOSERINES AND PHARMACEUTICAL COMPOSITIONS USEFUL AS CYTOSTATIC AGENTS

[75] Inventors: Hans Brachwitz; Reinhild Schönfeld; Peter Langen, all of Berlin, Fed. Rep. of Germany; Friedrich Paltauf; Albin Hermetter, both of Graz, Austria

[73] Assignee: Hafslund Nycomed Pharma Aktiengesellschaft, Linz, Austria

[21] Appl. No.: 598,607

[22] PCT Filed: Apr. 13, 1989

[86] PCT No.: PCT/EP89/00393

§ 371 Date: Oct. 19, 1990

§ 102(e) Date: Oct. 19, 1990

[87] PCT Pub. No.: WO89/10370

PCT Pub. Date: Nov. 2, 1989

[30] Foreign Application Priority Data

Apr. 19, 1988 [DE] Fed. Rep. of Germany ....... 3148688
Jul. 27, 1988 [DE] Fed. Rep. of Germany ....... 3183594

[51] Int. Cl.$^5$ .......................... A61K 31/66; C07F 9/40
[52] U.S. Cl. ................... 514/114; 514/119; 558/169; 558/170
[58] Field of Search ................. 558/169; 514/114

[56] References Cited

U.S. PATENT DOCUMENTS 4,751,320  6/1988  Masuda et al. ........... 558/169
4,916,249  4/1990  Brachwitz et al. ........ 558/169

FOREIGN PATENT DOCUMENTS 3606633  9/1987  Fed. Rep. of Germany.

OTHER PUBLICATIONS

Doerr, I. L. et al. Chemistry and Physics of Lipids vol. 19, pp. 185-202 (1977).

*Primary Examiner*—Mary C. Lee
*Assistant Examiner*—Michael G. Ambrose
*Attorney, Agent, or Firm*—Wenderoth, Lind & Ponack

[57] ABSTRACT

Compounds of formula I

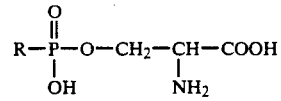

in which R denotes a straight-chain or branched, saturated or unsaturated aliphatic hydrocarbon radical having 6-30 C atoms wich may optionally be substituted by halogen or the radicals $OR_1$, $SR_1$ or $NR_1R_2$, where $R_1$ and $R_2$ in each case denote a hydrogen atom or an alkyl or acyl radical having 1-6 C atoms which have excellent virustatic and cytostatic action.

4 Claims, No Drawings

ALKYLPHOSPHONOSERINES AND PHARMACEUTICAL COMPOSITIONS USEFUL AS CYTOSTATIC AGENTS

DESCRIPTION

The invention relates to novel alkylphosphonoserines, processes for their preparation and their use.

A process for the preparation of alkylphosphocholines is described in R. Hirt, R. Berchthold Pharmaceutica Acta Helvetica, 33 (1958), 349–356 The cytostatic activity and the toxicity of hexadecylphophocholine is described in H. R. Scherf et al., Lipids 22, (1987), 927–929, and in C. Muschol et al. Lipids 22, (1987) 930–934.

It has now been possible to find novel alkylphosphonoserines which have an excellent cytostatic and virustatic action.

The invention relates to compounds of the formula I

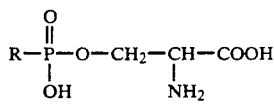

in which R denotes a straight-chain or branched, saturated or unsaturated aliphatic hydrocarbon radical having 6–30 C atoms which may optionally be substituted by halogen or the radicals $OR_1$, $SR_1$ or $NR_1R_2$, where $R_1$ and $R_2$ in each case denote a hydrogen atom or an alkyl or acyl radical having 1–6 C atoms.

In the formula I, R denotes a straight-chain or branched, saturated or unsaturated aliphatic hydrocarbon radical having 6–30 C atoms, preferably having 10–25 C atoms. Examples of such radicals are decyl, dodecyl, tetradecyl, hexadecyl, octadecyl, arachyl and 17-methyl-n-octadecyl radicals or the cis-9-n-octadecenyl radical.

These radicals may also be substituted by halogen, for example by Cl, Br, F or by the radicals $OR_1$, $SR_1$ or $NR_1R_2$. $R_1$ and $R_2$ in this case independently of one another denote hydrogen or an alkyl or acyl radical having 1–6 C atoms, for example a methyl, ethyl, n-propyl, i-propyl, n-butyl, i-butyl, pentyl or hexyl radical or, for example, a formyl, acetyl, propionyl, butyryl or i-butyryl radical.

The alkylphosphonoserines have certain structural relationships to physiologically active naturally occurring phospholipids, for example phosphatidylserines. However, they differ from these in that they contain no glycerol component. In comparison to the naturally occurring phosphatidylserines, the alkylphosphonoserines according to the invention have a higher biostability. They are potential cytostatics and virustatics.

The novel alkylphosphonoserines can be prepared by a process in which a) a compound of the formula II

in which R has the abovementioned meaning and A and B denote a hydroxyl group or, if desired, the salts of these compounds are reacted with a serine derivative of the formula III

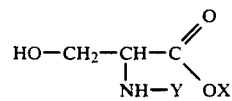

in which X denotes benzyl, t-butyl, phthalimidomethyl, isopropyl or benzhydryl, Y denotes N-benzoyloxycarbonyl, N-t-butoxycarbonyl or N-phthaloyl, if appropriate in the presence of a condensing agent, to give compounds of the formula IV

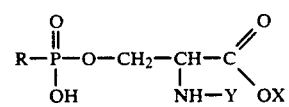

the protecting groups are removed and, if desired, the product is converted into a salt or b) a compound of the formula V

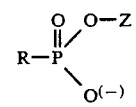

in which R has the abovementioned meaning and Z denotes an alkyl radical having 1–6 C atoms, which may optionally be substituted by Cl, Br or F or denotes the radicals

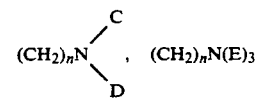

in which C and D independently of one another denote H or methyl and E denotes methyl and n denotes 2–6, is reacted with L-serine in the presence of phospholipase D.

The compounds of the formula II used as starting compounds can be prepared in a manner known per se by first synthesizing the dimethyl alkylphosphonates from the corresponding alkyl bromide R-Br and trimethyl phosphite, converting these into the trimethylsilyl esters by reaction with a mixture of trimethylsilyl chloride and sodium iodide and hydrolyzing these by the action of water.

The reaction of the compounds of the formula II is in general carried out by converting the compounds into the salt of a base, for example pyridine, and then reacting this salt with the serine derivative. The reaction is preferably carried out in the presence of a condensing agent, for example in the presence of 2,4,6-triisopropylbenzenesulphonyl chloride under anhydrous conditions and preferably in the presence of an inert organic solvent. A suitable solvent is, for example, pyridine.

The reaction components are customarily employed in equimolar amounts, but is also possible to employ up to a four molar excess of serine derivative.

The reaction is carried out at temperatures of about 5°–60° C., preferably at room temperature. After completion of the reaction, the acid chloride still present is destroyed in a customary manner, for example by adding water to the reaction solution, and the product is isolated in a customary manner, for example by extraction with diethyl ether. If desired, the compounds of the formula IV thus obtained can be further purified before the removal of the protecting groups, for example by column chromatography on silica gel. However, it is also possible to convert them without further purification into the compounds of the formula I.

For this purpose, the protecting groups are removed in a customary manner, for example by catalytic hydrogenolysis, hydrazinolysis or treatment with HCl or formic acid, preferably in an inert solvent. The compounds of the formula I can then be isolated in a known manner and, if desired, further purified, for example by chromatography.

The alkylphosphonoserines according to the invention can also be prepared by an enzymatic route. In this connection, compounds of the formula V are reacted with L-serine in the presence of phospholipase D. For this purpose, a solution or suspension of the compounds of the formula V is reacted with an excess of L-serine in an aqueous buffer system, for example in an acetate or tris buffer solution, at pH values of about 4–8.5, preferably 5–6, particularly preferably 5.6, in the presence of about 0.01—0.1 M CaCl$_2$ and in the presence of phospholipase D with the addition of diethyl ether or a mixture of diethyl ether with a further organic solvent, for example chloroform.

The reaction is carried out at temperatures of about 5°–60° C., preferably 35°–45° C. The reaction mixture is intensively stirred or shaken during the reaction. The duration of the reaction is about 0.5–48 hours. After reaction is complete, the enzyme phospholipase D is deactivated, for example by addition of a 0.1M EDTA solution and the compounds of the formula I are isolated in a customary manner.

The novel alkylphosphonoserines have a strong cytostatic and virustatic action. In order to determine the cytostatic action, the antiproliferative action was investigated in Ehrlich ascites tumor cells. It can be seen here that the compounds according to the invention have excellent cytostatic action. They can therefore be employed as cytostatics or virustatics, alone or in a mixture with other active substances, in the form of customary pharmaceutical preparations.

The compounds of the formula I are intended for use in humans and can be administered in a customary manner, for example orally or parenterally. They are preferably administered orally, the daily dose being about 0.05 to 20 mg/kg of body weight, preferably 0.05–5 mg/kg of body weight. However, depending on the general conditions and the age of the patient, the corresponding compound of the formula I, the nature of the disease and the manner of formulation, the treating physician can also prescribe lower or higher doses outside this range.

The compounds of the formula I can be administered alone or in combination with other pharmaceutically active substances, the content of the compounds of the formula I being between 0.1 and 99%. In general, the pharmaceutically active compounds are present in a mixture with suitable inert auxiliaries and/or excipients or diluents, for example pharmaceutically acceptable solvents, gelatin, gum arabic, lactose, starch, magnesium stearate, talc, vegetable oils, polyalkylene glycol, petroleum jelly or the like. The pharmaceutical preparations can be present in solid form, for example as tablets, coated tablets, suppositories, capsules and the like, in semi-solid form, for example as ointments or in liquid form, for example as suspensions or emulsions. If desired, they are sterilized and contain auxiliaries such as preservatives, stabilizers and emulsifiers, salt for changing the osmotic pressure and the like. Pharmaceutical preparations can in particular contain the compounds according to the invention in combination with other therapeutically useful substances. The compounds according to the invention can be formulated with these, for example together with the abovementioned auxiliaries and/or excipients or diluents, to give combination preparations.

EXAMPLE 1 n-Hexadecylphosphono-L-serine
n-Hexadecylphosphonic acid

A mixture of n-hexadecyl bromide (4.89 g, 16 mmol) and freshly distilled trimethyl phosphite (2.48 g, 20 mmol) is stirred at 116° C. for 24 hours. The excess trimethyl phosphite is then removed by distillation in vacuo and the residue is stored over phosphorus pentoxide in vacuo for 24 hours. The corresponding dimethyl n-hexadecylphosphonate is isolated from the residue by extracting twice with 10 ml of methanol each time. The two methanol extracts are combined and concentrated in vacuo. The oily colorless residue thus obtained, which still contains n-hexadecyl bromide in addition to the methyl n-hexadecylphosphonate, is further reacted with trimethylsilyl chloride (1.02 g, 9.4 mmol) and sodium iodide (1.4 g, 9.4 mmol) in 4.7 ml of anhydrous acetonitrile. The reaction is carried out with stirring at room temperature and lasts 15 minutes.

The sodium chloride formed in the reaction is filtered off. The filtrate is concentrated in vacuo and 4 ml of water are added to the resulting residue, n-hexadecylphosphonic acid being formed by hydrolysis. In order to remove the Me$_3$SiOSiMe$_3$ simultaneously formed, the mixture is subsequently distilled in vacuo several times with ethanol/water (1:1, v/v). After treatment of the residue with 7 ml of dry acetone, 346 mg of n-hexadexylphosphonic acid II are obtained. TLC (silica gel 60, Merck prepared plates, chloroform/methanol/water 65:25:4, v/v/v): Rf=0.15.

Elemental analysis calculated for C$_{16}$H$_{35}$PO$_3$ (306.42): C 62.71, H 11.51; found C 62.81, H 11.89 (%).

n-Hexadecylphosphono-N-t-butoxycarbonyl-L-serine benzhydryl ester

A solution of 92 mg (0.3 mmol) of n-hexadecylphosphonic acid in 1 ml of pyridine is concentrated in vacuo and the pyridinium salt thus obtained is subsequently dried over phosphorus pentoxide in vacuo. It is then dissolved in 5 ml of anhydrous pyridine. 356 mg (0.96 mmol) of protected serine (X=CH(C$_6$H$_5$)$_2$, Y=-CO—O—C(CH$_3$)$_3$), dried over phosphorus pentoxide in vacuo, are dissolved in 4 ml of anhydrous pyridine. The two solutions are mixed and 581 mg (1.92 mmol) of triisopropylbenzenesulfonyl chloride are added to the mixture. The reaction mixture is stirred under anhydrous conditions at room temperature for 24 hours. The mixture is then concentrated in vacuo and subsequently distilled several times with toluene, and the residue is dried over phosphorus pentoxide in vacuo. The residue is then extracted with 15 ml of diethyl ether and subsequently washed three times with 4 ml of diethyl ether. The ether solutions are combined and concentrated in vacuo. 118 mg of the n-hexadecylphosphonoserine derivative IV are obtained by recrystallization from acetonitrile of the residue thus obtained. A further purification is carried out by column chromatography on 8 g of silica gel 60 (particle size 0.04–0.063 mm, 230–400 mesh, Merck).

The chloroform used for the chromatography and the solvent mixtures for the elution contain 0.5% aqueous 25% strength ammonia. Elution is carried out using 50 ml of chloroform, 50 ml of chloroform/methanol 98:2, v/v, 200 ml of chloroform/methanol 95:5, v/v and 200 ml of chloroform/methanol 90:10, v/v. The fraction size is 15 ml. Fractions 15–20 contain 72 mg of pure hexadecylphosphono-N-t-butoxycarbonyl-L-serine benzhydryl ester. TLC (silica gel 60, Merck prepared plates, chloroform/methanol 80:20, v/v): Rf=0.2.

Elemental analysis calculated for $C_{37}H_{61}N_2PO_7$ ($NH_4$ salt, 676.87):

C 65.65, H 9.08, N 4.14; found C 65.44, H 9.15, N 3.73 (%).

n-Hexadecylphosphono-L-serine 69 mg (0.1 mmol) of the compound described are dried in vacuo over phosphorus pentoxide and subsequently dissolved in 13 ml of anhydrous chloroform. Dry nitrogen is passed through this solution for 10 minutes and hydrogen chloride gas is subsequently passed through the solution under anhydrous conditions at 0° C. for 20 minutes. The reaction vessel is then firmly closed and further stirred at 0° C. for 1 hour. In order to remove the hydrogen chloride gas, nitrogen is subsequently passed through the reaction mixture for 1 hour at room temperature. The reaction mixture is then concentrated in vacuo and a mixture of 10 ml of chloroform/methanol 2:1, v/v, 1 ml of water and 0.02 ml of 25% strength aqueous ammonia is then added to the residue, the mixture is shaken and, after phase separation, the organic phase obtained is separated off. The aqueous phase is extracted three times using 5 ml of chloroform/methanol/water 2:1:0.18, v/v/v, each time, and the organic solutions are combined and concentrated in vacuo. In order to remove residual water, the residue is subsequently distilled several times with 1 ml of benzene/ethanol 2:3, v/v. The product obtained, hexadecylphosphono-L-serine I, is dried over phosphorus pentoxide in vacuo and then washed with acetone.

Yield: 43 mg (95%).

In order to remove traces of ammonium chloride, the substance is chromatographed on 2.2 g of silica gel 60 (particle size 0.04–0.063 mm, 230–400 mesh, Merck). The column is equilibrated using chloroform/methanol/aqueous 25% strength ammonia 80:20:0.5, v/v/v. Elution is carried out using 20 ml of chloroform/methanol/aqueous 25% strength ammonia 80:20:0.5, v/v/v, 20 ml of chloroform/methanol/aqueous 25% strength ammonia 75:25:0.5, v/v/v, 20 ml of chloroform/methanol/aqueous 25% strength ammonia 70:30:0.5, v/v/v, 20 ml of chloroform/methanol/aqueous 25% strength ammonia 65:35:0.5, v/v/v and 200 ml of chloroform/methanol/aqueous 25% strength ammonia 60:40:0.5, v/v/v. The compound is obtained from fractions 7–19 by concentration. (Fraction size 20 ml).

TLC (silica gel 60, Merck prepared plates, chloroform/methanol/acetone/acetic acid/water 10:2:4:2:1, v/v/v/v/v): Rf=0.1.

Visualization is carried out using molybdate reagent and using ninhydrin reagent.

Elemental analysis calculated for $C_{19}H_{45}N_2PO_6$ ($NH_4$ salt, monohydrate, 428.55):

C 53.24, H 10.58, N 6.54; found C 53.80, H 10.55, N 5.73 (%).

FAB mass spectrometry:

Anion spectrum: m/e 414, $(M-2H+Na)^-$; m/e 392, $(M-H)^-$; m/e 305 $(M-CH_2CH(NH_2)COOH)^-$;

Cation spectrum: m/e 416, $(M+Na)^+$; m/e 438, $(M+2Na)^+$.

EXAMPLE 2 n-Hexadecylphosphono-L-serine 0.8 g of L-serine (7.6 mmol) is dissolved in 1.52 ml of 0.1M acetate buffer (pH 5.6), which is 0.09M in $CaCl_2$, at 45° C. 31 mg (0.075 mmol) of n-hexadecylphosphonocholine, 1.6 ml of diethyl ether/chloroform (9:1, v/v, ethanol-free) and 200 mg of a phospholipase D enzyme preparation which has been prepared from white cabbage and has an activity of 0.9 U/ml (1 unit (U) converts 1 μmol of substrate per minute at 27° C.) in the reaction mixture, are added to this solution. The mixture is stirred at 45° C. for 2.2 hours. After cooling to room temperature, 3.31 ml of 0.1M EDTA solution are added and the organic solvents are removed by passing in nitrogen. The aqueous phase which remains is stirred with 4.3 times its volume of chloroform/methanol (5:8, v/v) for 30 minutes and the undissolved material (L-serine) is filtered off with suction. 1 volume of water and 3.7 volumes of chloroform are added to the filtrate, the mixture is shaken for 10 minutes, the organic phase is separated off and concentrated in vacuo, and the residue obtained is separated by column chromatography on carboxymethyl cellulose (CM 52 Whatman, $Na^+$ form) Elution is carried out successively with 75 ml of chloroform, 300 ml each of chloroform/methanol 9:1, 8:2 and 7:3, then 1,750 ml of chloroform/methanol 1:1 (in each case v/v). The fraction size is 50 ml. 5 mg of pure n-hexadecylphosphono-L-serine (I, $R=C_{16}H_{33}$) are obtained from fractions 20–39.

TLC (silica gel 60, Merck prepared plates, $CHCl_3/CH_3OH$/acetone/acetic acid/$H_2O$ 50:10:20:10:5, v/v/v/v/v: Rf=0.1.

Further compounds were prepared in an analogous manner.

The following compounds were prepared analogously to Example 1.

EXAMPLE 3 n-Decylphosphono-L-serine

From n-decylphosphonic acid and protected serine (formula III, $X=CH(C_6H_5)_2$, $Y=CO-OC(CH_3)_3$. TLC (silica gel 60, Merck prepared plates, chloroform/methanol/acetone/acetic acid/water 10:2:4:2:1; v/v/v/v/v): Rf=0.1.

EXAMPLE 4 n-Dodecylphosphono-L-serine

From n-docecylphosphonic acid and protected serine (formula III, $X=CH(C_6H_5)_2$, $Y=CO-OC(CH_3)_3$. TLC (silica gel 60, Merck prepared plates, chloroform/methanol/acetone/acetic acid/water 10:2:4:2:1; v/v/v/v/v): Rf=0.1.

EXAMPLE 5 n-Tetradecylphosphono-L-serine

From n-tetradecylphosphonic acid and protected serine (formula III, $X=CH(C_6H_5)_2$, $Y=CO-OC(CH_3)_3$. TLC (silica gel 60, Merck prepared plates, chloroform/methanol/acetone/acetic acid/water 10:2:4:2:1; v/v/v/v/v): Rf=0.1.

EXAMPLE 6 n-Octadecylphosphono-L-serine

From n-Octadecylphosphonic acid and protected serine (formula III, X=CH(C$_6$H$_5$)$_2$, Y=CO—OC(CH$_3$)$_3$ TLC (silica gel 60, Merck prepared plates, chloroform/methanol/acetone/acetic acid/water 10:2:4:2:1; v/v/v/v/v): Rf=0.1.

EXAMPLE 7

Arachylphosphono-L-serine

From arachylphosphonic acid and protected serine (formula III, X=CH(C$_6$H$_5$)$_2$, Y=CO-OC(CH$_3$)$_3$. TLC (silica gel 60, Merck prepared plates, chloroform/methanol/acetone/acetic acid/water 10:2:4:2:1; v/v/v/v/v): Rf=0.1.

EXAMPLE A

Concentration-dependent Inhibition of Growth of Ehrlich Ascites Tumor Cells

| Concentration (M) | 1 × 10$^{-4}$ | 3 × 10$^{-5}$ | 1 × 10$^{-5}$ | 3 × 10$^{-6}$ |
| --- | --- | --- | --- | --- |
| Inhibition (%) | | | | |
| n-Hexadecyl phosphono-L-serine | 89 | 45 | 13 | 9 |

We claim:
1. Compounds of the formula I

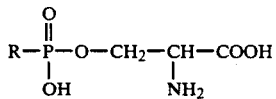

in which R denotes a straight-chain or branched, saturated or unsaturated aliphatic hydrocarbon radical having 6—30 C atoms which may optionally be substituted by halogen or the radicals, OR$_1$, SR$_1$ or NR$_1$R$_2$, where R$_1$ and R$_2$ in each case denote a hydrogen atom or an alkyl or acyl radical having 1-6 C atoms.

2. Compounds of the formula I

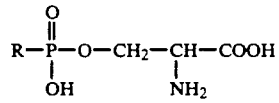

according to claim 1, in which R denotes a straight-chain or branched, saturated or unsaturated aliphatic hydrocarbon radical having 10–25 C atoms which may optionally be substituted by halogen or the radicals OR$_1$, SR$_1$ or NR$_1$R$_2$, where R$_1$ and R$_2$ in each case denote a hydrogen atom or an alkyl or acyl radical having 1-6 C atoms.

3. n-Hexadecylphosphono-L-serine [sic].

4. A pharmaceutical composition, containing compounds of the formula I

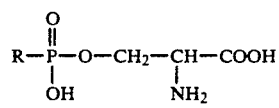

in which R denotes a straight-chain or branched, saturated or unsaturated aliphatic hydrocarbon radical having 6—30 C atoms which may optionally be substituted by halogen or the radicals OR$_1$, SR$_1$ or NR$_1$R$_2$, where R$_1$ and R$_2$ in each case denote a hydrogen atom or an alkyl or acyl radical having 1-6 C atoms, in combination pharmaceutical auxiliaries, excipients and/or diluents.

* * * * *